(12) United States Patent
Kadavy et al.

(10) Patent No.: US 6,436,111 B1
(45) Date of Patent: Aug. 20, 2002

(54) EXPANDABLE ATHERECTOMY BURR (75) Inventors: Thomas D. Kadavy, Bellevue; Eric W. Baker, Seattle; Thomas J. Hiblar, Everett; Kurt M. Laundroche, Snohomish, all of WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/742,767

(22) Filed: Dec. 19, 2000

(51) Int. Cl.⁷ .............................................. A61B 17/32
(52) U.S. Cl. ....................................................... 606/159
(58) Field of Search ........................... 606/1, 108, 199, 606/170, 171, 180; 604/22

(56) References Cited

U.S. PATENT DOCUMENTS

| 4,273,128 A | 6/1981 | Lary |
| 4,950,277 A | 8/1990 | Farr |
| 4,966,604 A | 10/1990 | Reiss |
| 5,019,088 A | 5/1991 | Farr |
| 5,019,089 A | 5/1991 | Farr |
| 5,030,201 A | 7/1991 | Palestrant |
| 5,100,425 A | 3/1992 | Fischell et al. |
| 5,192,291 A | * 3/1993 | Pannek, Jr. |
| 5,242,461 A | * 9/1993 | Kortenbach et al. |
| 5,667,490 A | 9/1997 | Keith et al. |
| 5,897,567 A | 4/1999 | Ressemann et al. |
| 5,938,670 A | 8/1999 | Keith et al. |
| 6,096,054 A | 8/2000 | Wyzgala et al. |
| 6,156,046 A | * 12/2000 | Passafaro et al. |

FOREIGN PATENT DOCUMENTS

| EP | 0 379 786 B1 | 3/1995 |
| WO | WO 99/44513 A2 | 9/1999 |

* cited by examiner

Primary Examiner—Scott M. Getzow
(74) Attorney, Agent, or Firm—Christensen O'Connor Johnson Kindness PLLC (57) ABSTRACT

An expandable atherectomy burr has numerous cutting elements that expand radially outward as the burr is rotated. The cutting elements can include arms or flaps that have an abrasive surface thereon and expand as the burr is rotated. In an alternative embodiment, the burr includes a stack of cutting disks, each of which includes cutting elements that expand as the burr is rotated in order to create variably sized lumens in a vessel.

13 Claims, 6 Drawing Sheets

EXPANDABLE ATHERECTOMY BURR

FIELD OF THE INVENTION

The present invention relates to medical devices, in particular to expandable atherectomy burrs for creating variably sized lumens in a vessel.

BACKGROUND OF THE INVENTION

Atherectomy is becoming a commonly accepted medical technique to remove deposits from a patient's vessel. In a typical atherectomy procedure, a guide catheter and guidewire are advanced through the patient's vasculature to the point of the occlusion. Next, a driveshaft having a burr at or near its distal end is advanced over the guidewire and the driveshaft is rotated at high speed to cause the burr to ablate deposits in the vessel. The diameter of the burr is less than the diameter of the guide catheter through which it is routed. Therefore, the size of the lumen that can be created in the vessel is also limited. If the physician wishes to create a larger lumen, another atherectomy burr with a larger diameter and perhaps a new guide catheter must be routed over the guidewire and the procedure is repeated. However, it is also well known that the risk of patient complications may increase as larger guide catheters are used. In addition, the use of multiple atherectomy burrs increases the cost and the time required to complete an atherectomy procedure. Therefore, there is a need for an atherectomy device that can create lumens in a vessel that are larger than the diameter of the guide catheter used to deliver the burr to the site of the occlusion.

SUMMARY OF THE INVENTION

The present invention is an atherectomy burr for creating variably sized lumens in a patient's vessel. The atherectomy burr includes a distal end, a proximal end and one or more cutting members that expand radially outward as the burr rotates. Each of the cutting members has a cutting surface that ablates occluding matter from the vessel as the burr is rotated. The invention also includes a variety of mechanisms to limit expansion of the cutting members.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
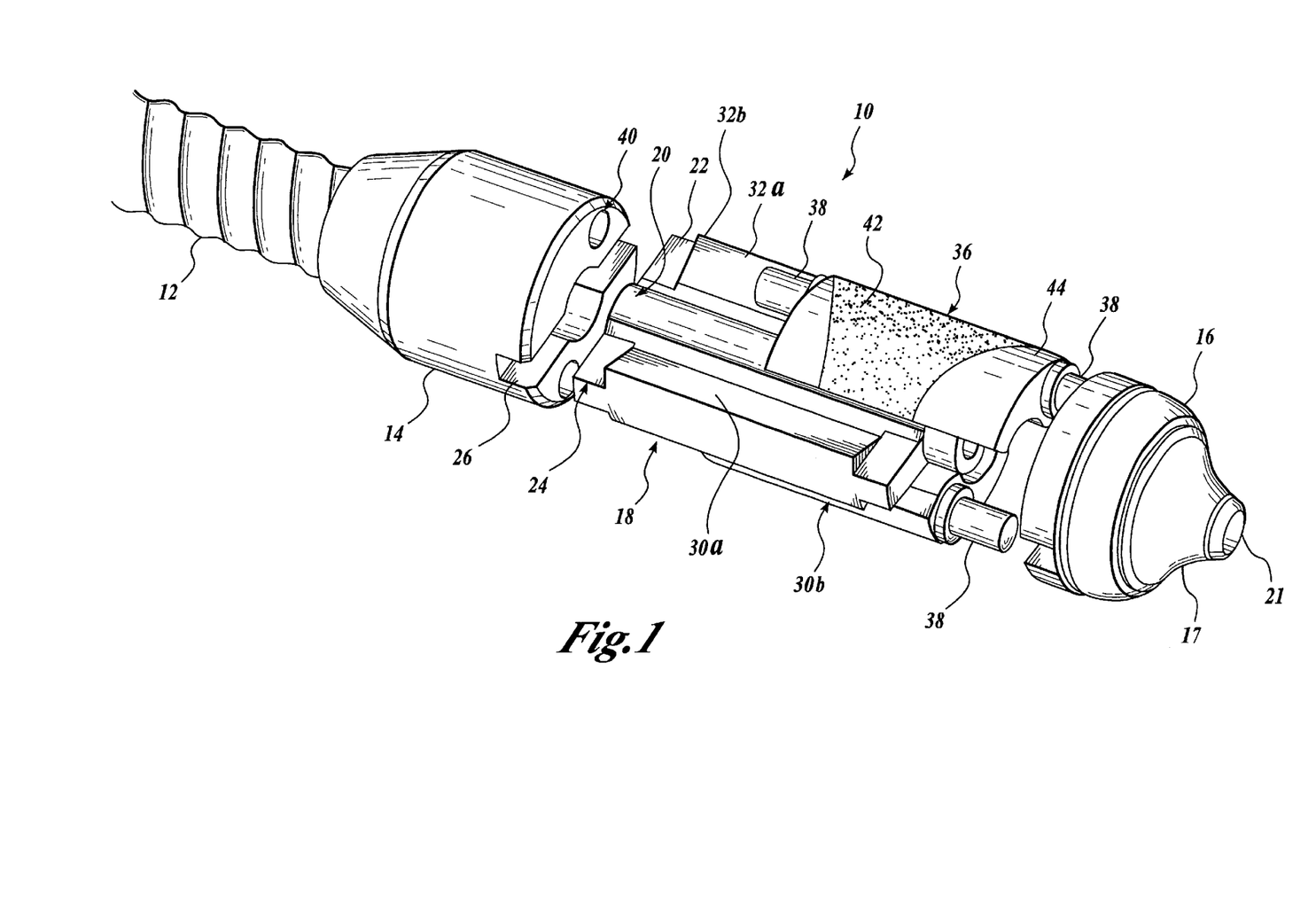
FIG. 1 is an isometric exploded view of an expandable atherectomy burr according to a first embodiment of the present invention.

FIG. 1 illustrates an expandable atherectomy burr 10 constructed in accordance with one embodiment of the present invention. The atherectomy burr 10 is secured to a driveshaft 12 which rotates the burr in order to remove deposits from a vessel. The atherectomy burr 10 includes a proximal end 14 having an opening (not shown) into which the driveshaft 12 is secured by a suitable technique such as with an adhesive or by welding. The ablation burr 10 also includes a distal end 16 having a relatively smooth a traumatic tip 17. The proximal end 14 of the burr is coupled to the distal end 16 with a connecting post 18. The connecting post 18 is formed as a center tube 20 having a pair of diametrically opposed side rails 22 and 24 that run along the length of the center tube 20. The end of the center tube 20 in combination with the side rails 22,24 form a key that fits within a corresponding keyway 26 in the proximal end 14 of the burr and a similar keyway that is formed within the distal end 16. The connecting post 18 is secured to the proximal end 14 and the distal end 16 of the burr by a suitable technique such as with an adhesive or by welding. In the space between the proximal end 14 and the distal end 16 of the burr, the side rails 22 and 24 have raised top and bottom edges 30a, 30b, 32a, 32b that provide camming surfaces as will be described in further detail below.

To provide a variable diameter cutting action, the burr 10 includes two or more expandable cutting members that are secured around the connecting post 18. In this embodiment, each cutting member is formed as a pair of outwardly swinging arms 36 that are secured by a pair of pins 38 that fit within a corresponding hole 40 in the proximal end of the burr 14 and a hole (not shown) in the rear surface of the distal end 16. The arms 36 are free to pivot radially outward on the pins 38. Each of the arms 36 has an arcuate or curved outer surface such that when the arms 36 are in their fully retracted state, the burr 10 has a cylindrical profile.

The outer surface of the arms 36 is at least partially covered with an abrasive or other suitable cutting surface. As the burr is rotated, the cutting surface on the arms 36 engages a lesion within the vessel and removes portions of the occluding matter. In addition, the distal and proximal ends of the outer surface of the arms may include a bevel 44 that helps to ensure the arms can be retracted to their closed position when the burr is withdrawn into the surrounding catheter.

When the burr 10 is rotated by the driveshaft 12, the arms 36 are expanded radially outward by the centrifugal force of rotation. The size of the arms in the area of the pins 38 and the size of the raised edges 30a, 30b, 32a, 32b on the side rails 24 cooperate to form stops which limit the extent to which the arms can travel radially outward.

Figure 2A:
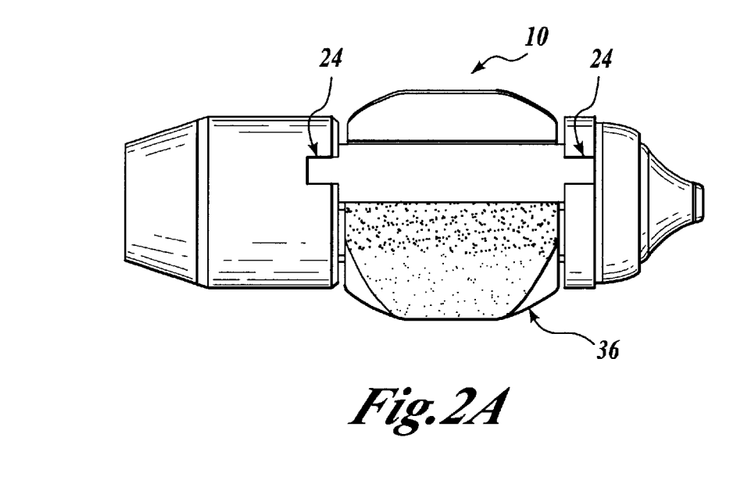
FIGS. 2A–2D illustrate the atherectomy burr shown in FIG. 1 in an open and closed state and how the effective cutting diameter changes as the burr is rotated.
Figure 2B:
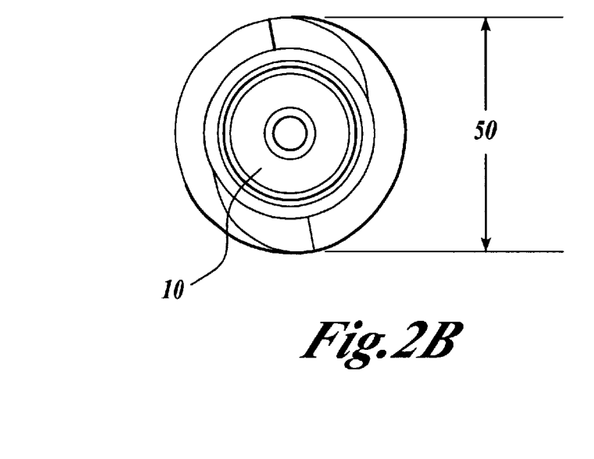
Figure 2C:
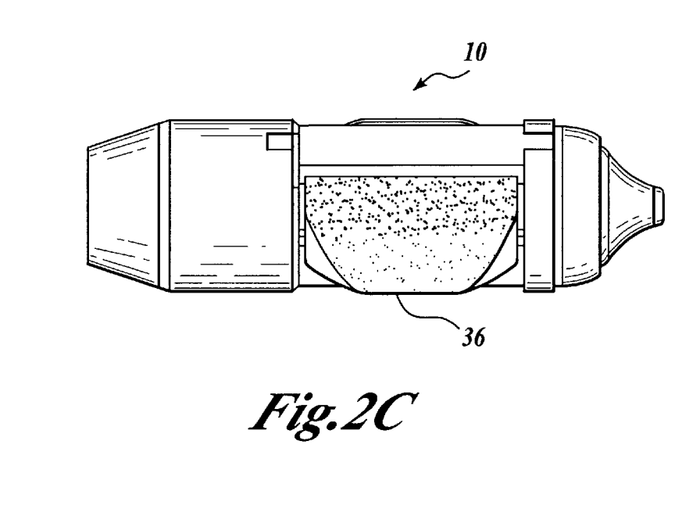
Figure 2D:
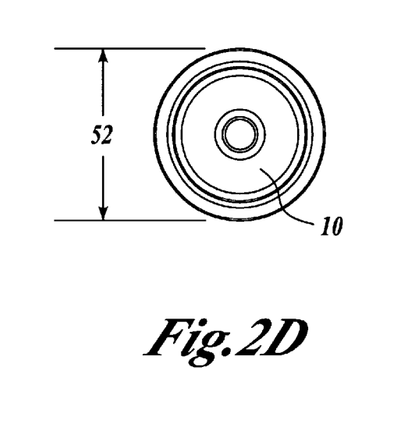

FIG. 2A illustrates the ablation burr 10 with the arms 36 fully extended. As shown in FIG. 2B, the effective cutting diameter of the burr, as indicated by the arrow 50, is larger than the cutting diameter of the burr when the arms 36 are in the fully retracted position as shown in FIG. 2C and as indicated by the arrow 52 shown in FIGS. 2D.

In operation, the physician advances the ablation burr 10 through a guide catheter having a diameter that is preferably just larger than the diameter of the burr 10 with the arms 36 in the retracted position. Once the ablation burr has been extended past the distal end of the guide catheter, rotational motion is applied to the driveshaft 12, such that the arms 36 begin expanding radially outward. The ablation burr 10 is passed through an occlusion in order to remove a portion of the occluding material from the vessel. If desired, aspiration may be applied to the guide catheter to remove ablated particles during the procedure. Each time the burr is passed through the occlusion, more material is removed and the arms 36 can extend further outwards until they reach the point of maximum diameter, thereby creating a maximum sized lumen in the vessel.

In the embodiment of the invention shown in FIG. 1, the arms 36 are preferably made from a relatively hard material such as plastic or metal by metal injection molding, casting, electro-discharge machining or electro forming. Metal injection molding for the arms 36 and the post 18 is the currently preferred manufacturing technique. Each arm has an inner surface 45 that fits around the circular tube 20 of the connecting post 18. It will be appreciated that with their design, the burr should be rotated such that the arms lead with the side having the pins 38. If the burr is rotated in the other direction, such that the free ends of the arms 36 lead, the burr may bind in the vessel.

As an alternative to the embodiment shown in FIGS. 1 and 2A–2D, the arms 36 may be made of an elastomeric sheet having one edge secured to the burr and a free end that can wrap around the circumference of the burr and expand radially outward when the burr is rotated. The elastomeric sheets can be plated with an abrasive as described in U.S. Pat. No. 6,096,054, which is incorporated by reference. By plating both sides of the sheet, the burr can be rotated in either direction.

Figure 3:
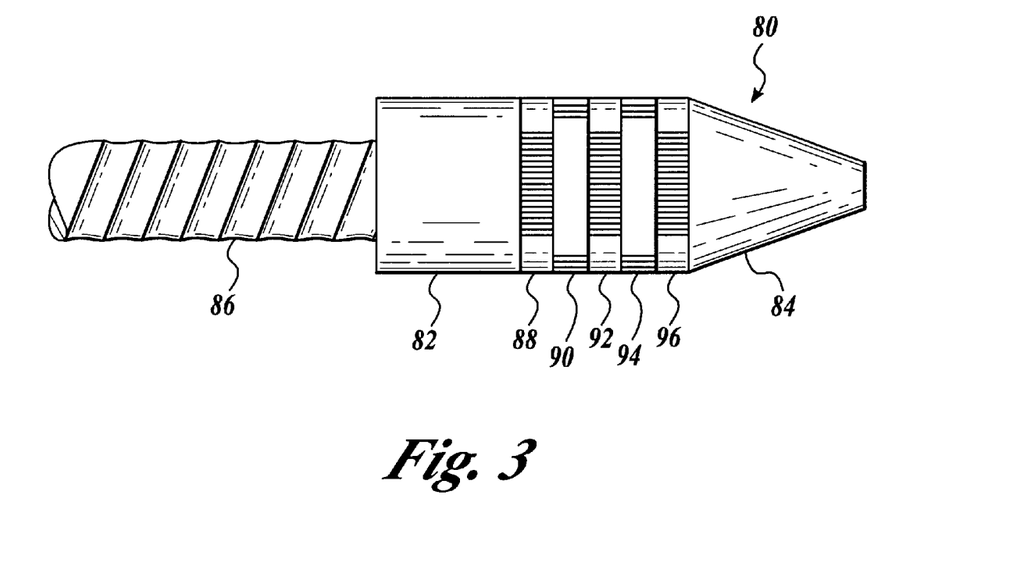
FIG. 3 illustrates an alternative embodiment of an expandable atherectomy burr including a number of expandable cutting members that are formed as disks according to another aspect of the present invention.

FIG. 3 illustrates an alternative embodiment of an expandable atherectomy burr in accordance with another aspect of the present invention. The atherectomy burr 80 includes a proximal end 82 and a distal end 84. The proximal end 82 is secured to a driveshaft 86 that rotates the burr in order to remove deposits from a patient's vessel.

Sandwiched between the proximal end 82 and the distal end 84 of the burr are a number of expandable cutting members 88–96 having abrasive or cutting surfaces that expand radially outward when the atherectomy burr 80 is rotated. The cutting surfaces of at least some of the cutting members are oriented in a different direction such that together the complete set of cutting members provide cutting surfaces that extend around the circumference of the burr.

Figure 4:
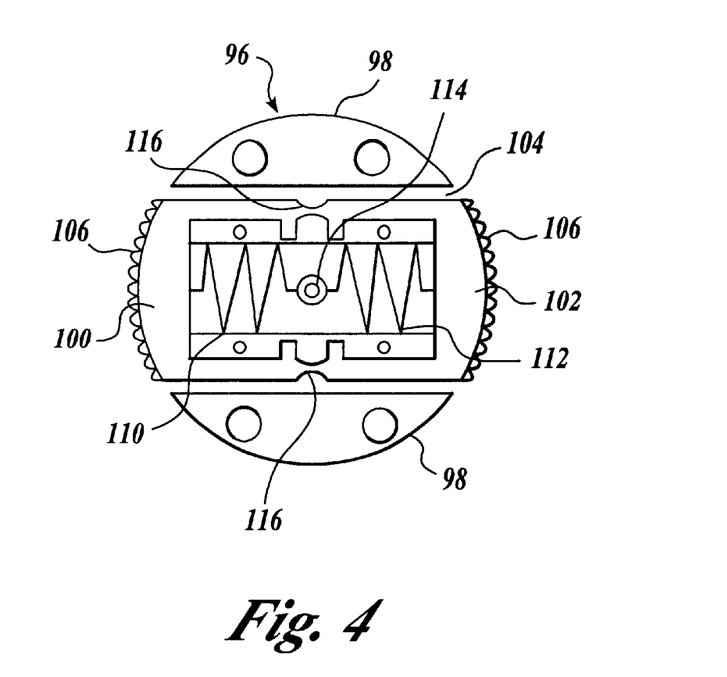
FIG. 4 illustrates a first embodiment of an expandable cutting disk according to the present invention.

FIG. 4 illustrates one -embodiment a cutting member according to the present invention. The cutting member is a disk 96 having a frame 98 in which guides a pair of cutting elements 100, 102 in a slot 104. The outermost edge of the cutting elements 100, 102 is etched or plated with an abrasive surface to form a series of teeth 106 that abrade occluding material in the vessel as the atherectomy burr is rotated. Each of the cutting elements 100, 102 is biased with a spring 110, 112 respectively. The springs are connected at one end to an inner surface of the cutting elements and to a hub 114 that is aligned with a hole 126 (FIG. 5) in the frame 98 to allow a guidewire to pass through the frame 98 and the cutting element. In one embodiment of the invention, the two cutting elements 100, 102 are connected together by a pair of mechanical fuses 116 that comprise thin regions of material joining the two cutting elements. When the burr is rotated with sufficient centrifugal force, the mechanical fuses 116 break, thereby allowing the two cutting elements 100, 102 to separate and expand radially outward within the slot 104. The centrifugal force is counteracted by the springs 110, 112 which operate to return the cutting elements 100, 102 towards the center of the burr after rotation of the burr has ceased.

Figure 5:
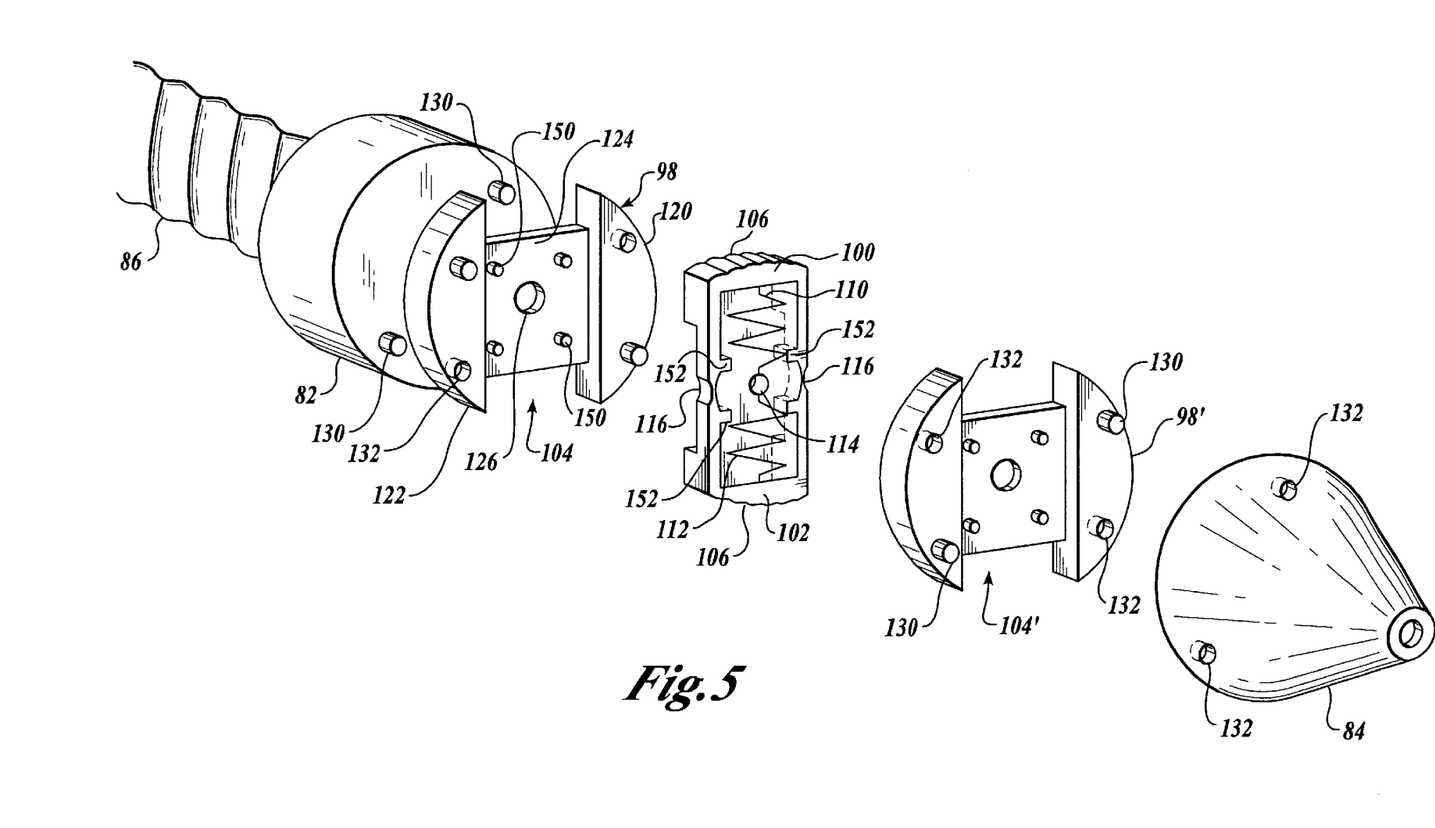
FIG. 5 is a partial, exploded isometric view of an expandable atherectomy burr constructed with a number of cutting disks of the type shown in FIG. 4.

FIG. 5 shows how the atherectomy burr 80 shown in FIGS. 3 and 4 is constructed. The frame 98 comprises two diametrically opposed, semi-circular sections 120, 122 that are separated by a flat plate 124, the thickness of the plate 124 is less than that of the semi-circular sections 120, 122 such that the area between the semi-circular sections forms the slot 104. The outer surfaces of the semi-circular sections 120, 122 are preferably smooth. However, if desired they may be plated with an abrasive material or etched to form a cutting surface in order to provide additional cutting action as the burr is rotated.

In order to secure the frame 98 to the proximal end 82 of the burr, the proximal end 82 includes a pair of posts 130 that are received in corresponding holes 132 formed in the rear surface of each of the semi-circular portions 120, 122. The front surface of the semi-circular portions 120, 122 also include a pair of posts 130. The posts 130 and the holes 132 on the semi-circular portions are oriented such that when another frame 98' is fitted onto the frame 98, the orientation of a slot 104' is rotated with respect to the slot 104. In this manner, each of the expandable cutting elements expand in different directions around the circumference of the burr.

As indicated above, the cutting elements 100, 102 fit within the slot 104 formed between the two semi-circular portions 120, 122 of the frame 98. Each of the cutting elements is a generally U-shaped structure with a convex outer cutting surface 106 and two parallel legs. To further prevent the over-expansion of the cutting elements, the plate 124 on the frame 98 includes a pair of posts 150 that engage inwardly extending tabs 152 on the legs of the cutting elements 100, 102. In operation, once the centrifugal force created by the rotation of the burr breaks the mechanical fuses 116 that join the legs of the cutting elements 100, 102, the cutting elements are free to slide radially outward within the slot 104 against the return force created by springs 110, 112. The maximum radial distance that the cutting elements can expand outward is limited by the strength of the springs 110, 112 and by the position of the tabs 152 and the posts 150 on the plate 124.

The burr 80 is created by a number of frames 98 each having a pair of cutting elements 100, 102 in the slots. The distal end 84 of the burr is secured to the posts 130 extending from the front surface of the distal most frame 98. The frame 98 and the cutting elements 100, 102 can be manufactured by a photolithographic process, electro forming, electro discharge machining or other processes known in the art to manufacture small mechanical parts.

In the embodiment of the invention shown in FIGS. 3–5, the frames 98 are secured to the proximal end 82 and the distal end 84 with the posts 130 and holes 132 found on each adjacent part. However, it will be appreciated that other mechanisms could be used. For example, the distal end 82 of the burr could be fitted with a mandrel over which the frames 98 are fitted, wherein the proximal end of the mandrel is affixed to the proximal end 82 of the burr. In addition, it will be appreciated that the mechanical fuses 116 allow the pair of cutting elements to be constructed as a single unit. However, the fuses could be eliminated and each cutting elements could be formed as a single piece.

Figure 6A:
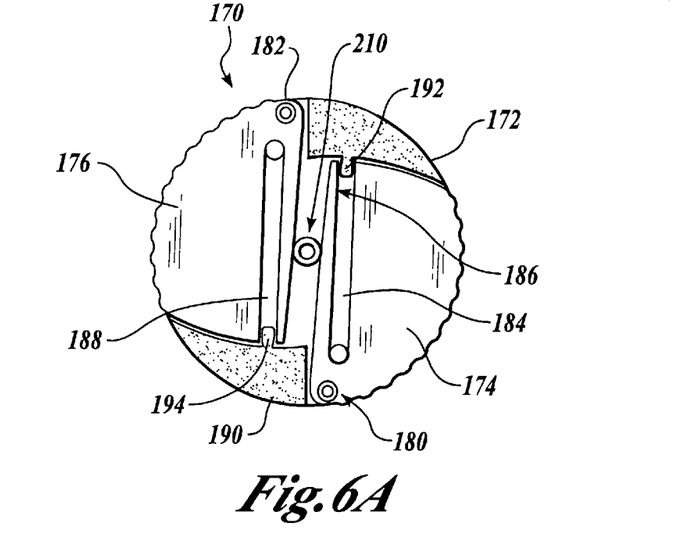
FIGS. 6A and 6B illustrate an alternative embodiment of an expandable cutting disk according to the present invention.
Figure 6B:
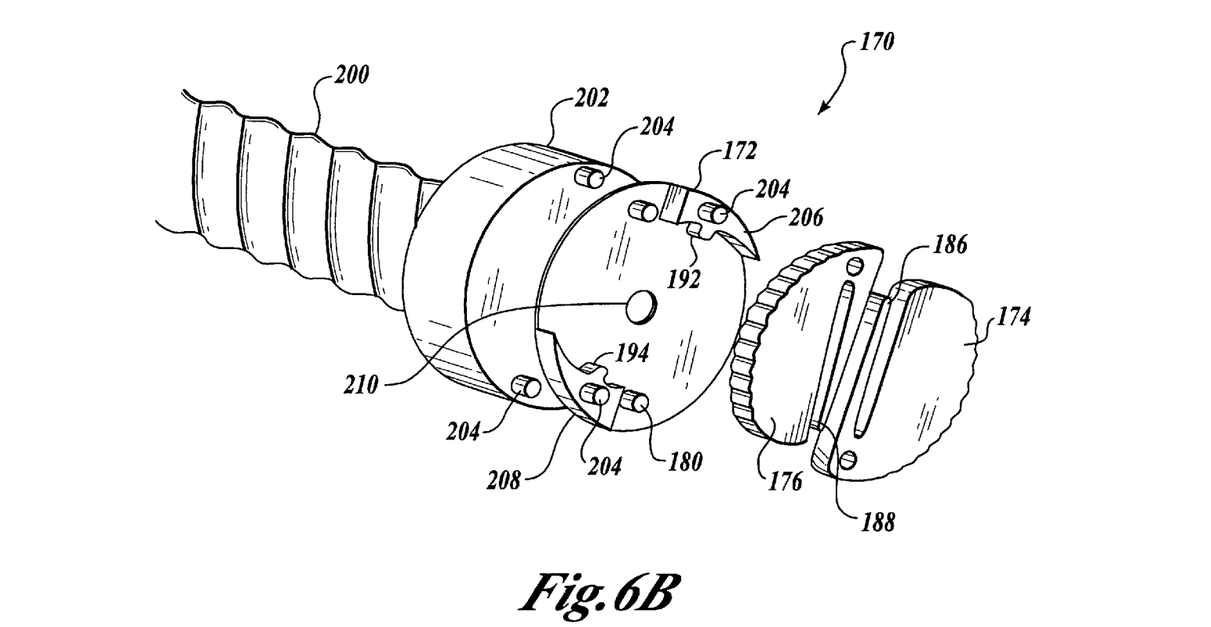

FIGS. 6A and 6B show another alternative embodiment of a cutting member in accordance with the present invention.

The cutting member comprises a disk 170 having a generally circular plate 172 on which are mounted a pair of cutting elements 174, 176. The cutting element 174 is positioned over a post 180 near the perimeter of the plate 172. Similarly, the cutting element 176 is positioned over a post 182 also positioned near the perimeter of the plate 172. When the burr is rotated, centrifugal force causes the cutting elements 174, 176 to rotate outwards on the posts 180, 182 thereby expanding the effective cutting diameter of the burr.

In order to limit the expansion of the burr, the cutting element 174 includes a slot 184 that extends adjacent an inner edge of the cutting element such that the space between the slot and the inner edge forms a leaf spring 186 that opposes the centrifugal force created when the burr is rotated. Similarly, the cutting element 176 includes a slot 188 that defines a leaf spring 190 near the inner edge of the cutting element 176. The plate 172 includes a pair of tabs 192, 194 that fit in the slots 184 and 188 respectively, to provide a point against which the leaf springs 186 and 188 are biased. During rotation of the burr, the cutting elements 174 and 176 are forced radially outward against the return force created by the interaction of the leaf springs 186, 190 and the tabs 192, 194.

FIG. 6B illustrates one method of constructing an ablation burr with the disks 170 as shown in FIG. 6A. The ablation burr includes a driveshaft 200 that is secured to proximal end 202 of the burr. The proximal end 202 includes a pair of posts 204 that are received in corresponding holes on the back surface of the plate 172. The plate 172 further includes a pair of diametrically opposed arcuate banks 206, 208 into which are formed the tabs 192, 194 respectively. The cutting elements 174, 176 are fitted between the banks 206, 208 and over the posts 180, 182 in order to form a complete cutting disk assembly. The plate 172 also includes a central aperture to intend to allow for a guidewire (not shown) to pass through the disk cluster.

To secure another disk to the burr, the banks 206, 208 also include a set of posts 204 that allow another cutting disk assembly to be secured to it in order to form a stack of expanding disk assemblies in a similar manner to that shown in FIG. 5. The distal end of the burr is preferably secured to the front face of the distalmost disk assembly.

Figures 7A, 7B, 8A, 8B:
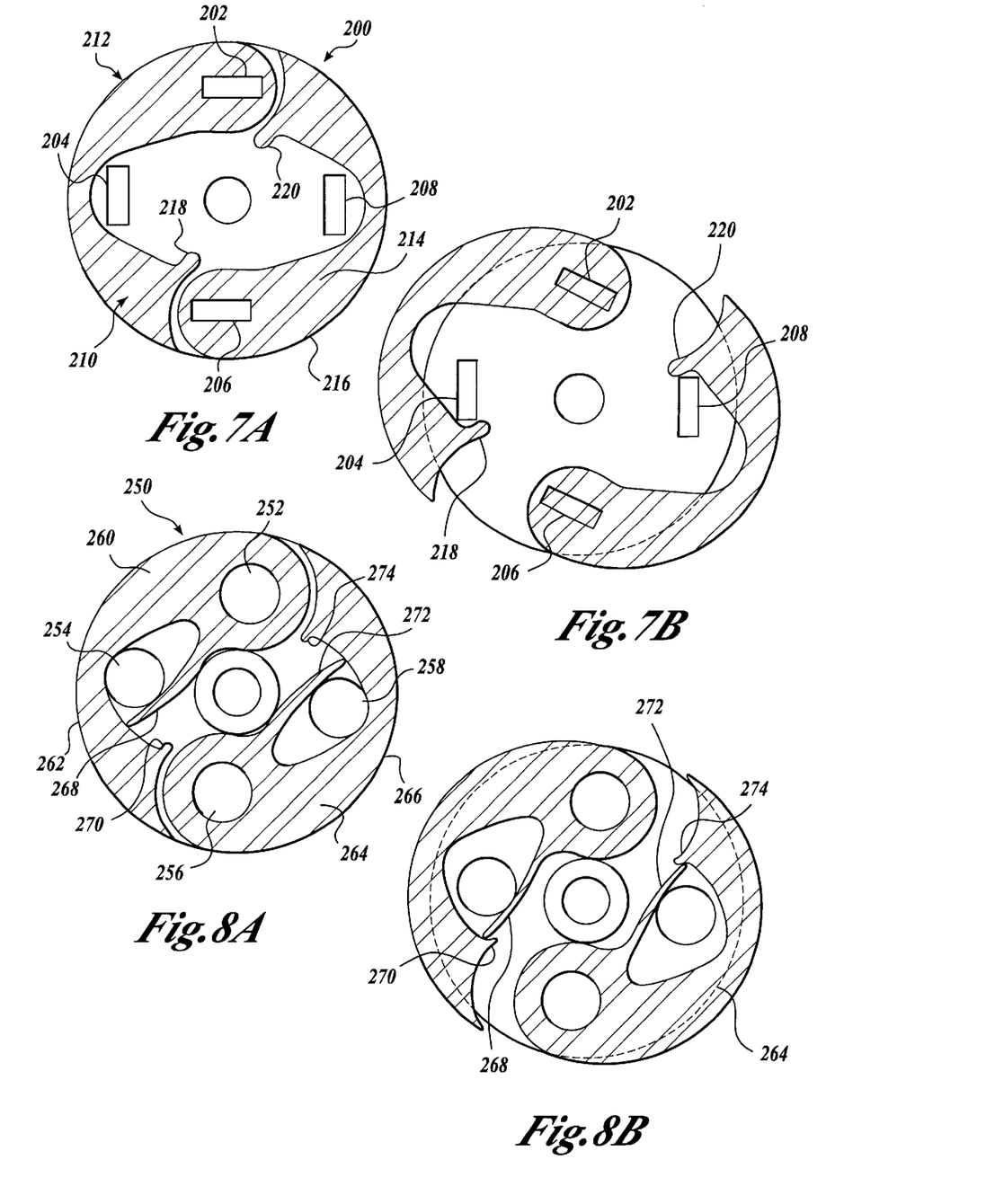
FIGS. 7A and 7B show another alternative embodiment of an expandable cutting disk according to the present invention.
FIGS. 8A and 8B illustrate another alternative embodiment of an expandable cutting disk according to the present invention.

FIGS. 7A and 7B illustrate another alternative embodiment of a cutting member in accordance with the present invention. In this embodiment, the burr includes a number of torsion springs 202, 204, 206, 208 disposed between a proximal end and distal end of the burr (not shown). Positioned over these torsion springs are a number of abrasive cutting members each of which comprises a pair of cutting elements 210, 214 having abrasive outer surfaces 212, 216 respectively. In the presently preferred embodiment of the invention, each of the torsion springs 202, 204, 206 and 208 comprises a metal strip that is rectangular in cross section and is equally spaced about the circumference of the burr. Each cutting element 210, 214 has a head end secured to a torsion spring and a tail end position adjacent the diametrically opposing torsion spring. The center portion of the cutting element extends on the outside of the intervening torsion spring. For example, the cutting element 210 has a head end secured to the torsion spring 202. The middle portion of the cutting element passes to the outside of the torsion spring 204 and the tail end of the cuffing element is positioned near the torsion spring 206. Similarly, the cutting element 214 has a head end secured to this torsion spring 206, a middle section that passes to the outside of the torsion spring 208 and a tail end that is positioned near the torsion spring 202. In the embodiment shown in FIGS. 7A and 7B, the cutting elements are coupled to the torsion springs such that they cannot rotate around the springs. In the embodiment shown, this is accomplished by having a rectangular slot in the cutting element that fits over the rectangular torsion spring. However, other cooperating shapes could be used to both prevent the cutting element from rotating around the spring while allowing the spring to twist.

As shown in FIG. 7B, when the ablation burr is rotated, the cutting elements 210, 214 twist the torsion springs such that the cutting elements can expand outwardly. The outward expansion of the cuffing elements is limited by the return force created by the twisting springs. In addition, each cutting element 210, 214, has a tab 218, 220 on its tail end that catches the intervening torsion spring 204, 208 as the cutting element expands outward to limit further expansion thereof.

To assemble an atherectomy burr with the cutting elements shown in FIGS. 7A, 7B, the torsion springs are inserted into corresponding slots in the proximal portion of the burr ad secured with an adhesive by welding. The torsion screws could also be made integral with either the proximal or distal end of the burr. Next, the cutting elements are positioned over the torsion springs in an alternating pattern such that the cutting elements expand in different directions during rotation of the burr. Finally, a distal end of the burr is secured to the torsion springs either by an adhesive, welding or other suitable fastening method.

FIGS. 8A and 8B illustrate yet another alternative embodiment of a cutting member, according to the present invention. In this embodiment, an ablation burr has a proximal end and distal end (not shown) that are secured together with a number of circular posts 252, 254, 256 and 258 which are preferably positioned at regular intervals around the circumference of the burr. Disposed over the circular posts are a number of cutting members 250, each comprising a pair of cutting elements 260 and 264. In the same manner as the embodiment shown in FIGS. 7A and 7B, each cutting element has a head end positioned over one of the circular posts and a tail end positioned adjacent an opposite circular post. For example, the cutting element 260 has a head end positioned over the post 252 and a tail end positioned adjacent the circular post 256. A majority of the middle portion of the cutting element 270 extends to the outside of the intervening circular post 254. Similarly, the cuffing element 264 has a head end positioned over the circular post 256 and a tail end positioned adjacent the circular post 252 and a middle portion, the majority of which is positioned to the outside of the intervening circular post 258.

In contrast to the embodiment shown in FIGS. 7A and 7B, the cutting elements are free to rotate around the circular posts 252, 256 but are biased by a leaf spring that is integral with the cutting elements but extends to the inside of the intermediate circular post. For example, the cutting element 260 has a leaf spring 270 that is positioned inside of the circular post 254. Similarly, the cutting element 264 has a leaf spring 272 that is positioned inside of the circular post 258. The cutting element 260 includes a tab 270 on its tail end that catches the end of the lead spring to prevent further expansion thereof. A similar tab 272 is disposed on the tail end of the cutting element 264.

As shown in FIG. 7B, when the burr is rotated, the cutting elements rotate about the circular posts 252, 256 and expand radially outward against the force of the leaf springs 268 and 272. The outer surfaces of the cutting surfaces are etched or have an abrasive surface plated thereon to provide a cutting surface to remove deposits from a vessel as the burr is rotated. To construct a burr using the cutting disks 250 as shown in FIGS. 8A and 8B, the cutting elements are placed over the circular posts 252, 254, 256 and 258 in a pattern such that the cutting elements expand outwardly in different directions. Once the cutting elements are in place, a distal end of the burr is secured to the posts.

It will be appreciated that each of the embodiments shown in FIGS. 6A, 6B, 7A, 7B and 8A, 8b are preferably rotated in a direction such that the point at which the cutting members are secured to the burr leads during rotation.

While the preferred embodiment of the invention has been illustrated and described, it will be appreciated that various changes can be made therein without departing from the scope of the invention. It is therefore intended that the scope of the invention be determined from the following claims and equivalents thereto.

The embodiments of the invention in which an exclusive property or privilege is claimed are defined as follows:

1. An atherectomy burr for removing deposits from a patient's vessel, comprising:

a burr body having a proximal end, a distal end and one or more arms rotatably coupled to the proximal and distal end of the burr, said one or more arms extending radially outward as the burr is rotated, each of the one or more arms having a cutting surface that ablates deposits in the vessel; and a stop on the burr to limit the outward expansion of the one or more arms.

2. The atherectomy burr of claim 1, wherein the one or more arms are rotatably coupled to the distal and proximal ends of the burr by posts about which the one or more arms can rotate.

3. The atherectomy burr of claim 2, wherein the stop includes a camming surface against which the one or more arms engage as they rotate on the posts.

4. The atherectomy burr of claim 3, wherein the one or more arms each has a beveled leading and trailing surface on the outer cutting surface.

5. An atherectomy burr, comprising:

a burr body having a proximal end, a distal end and a number of cutting disks disposed between the proximal and distal end; each of the cutting disks having cutting elements that expand radially outward as the burr is rotated, wherein each cutting element has a cutting surface that removes deposits from a patient's vessel.

6. The atherectomy burr of claim 5, wherein each of the cutting elements includes a leaf spring that engages a fixed point on the burr to bias the cutting elements radially inward.

7. The atherectomy burr of claim 5, wherein the cutting elements are secured together with a mechanical fuse that separates when the burr is rotated to allow the cutting elements to expand radially outward.

8. The atherectomy burr of claim 5, wherein each of the cutting elements is coupled to a torsion spring that biases the cutting elements radially inward as the burr is rotated.

9. An atherectomy burr that creates variable sized lumens in a vessel, comprising:

a drive shaft;

a burr body having a proximal end and a distal end coupled to the driveshaft and a number of stacked expandable cutting elements positioned transverse to a longitudinal axis of the burr, that create a lumen in a vessel as the burr is rotated by the driveshaft; and means for limiting the expansion of the cutting elements as the burr is rotated.

10. An atherectomy burr, comprising:

a burr body having a proximal end and a distal end and a connecting post that joins the proximal end and the distal end;

two or more arms rotatably secured to the proximal and distal ends of the burr body, each arm having an exterior cutting surface that extends generally parallel to the connecting post;

wherein said burr body is rotatable by a driveshaft such that the two or more arms extend radially outward to create a variably sized lumen in a patient's vessel.

11. An atherectomy burr, comprising:

a burr body having a proximal end, a distal end and a number of disks stacked between the proximal end and the distal end; each disk having two or more cutting elements that expand radially outwards as the burr body is rotated by a driveshaft, each cutting element being biased radially inwards to limit the expansion thereof.

12. An atherectomy burr of claim 11, wherein each of the cutting elements rotates outwardly around a post that extends between the proximal and distal end of the burr.

13. The atherectomy burr of claim 11, wherein each of the cutting elements is secured to a torsion spring that extends between the proximal and distal ends of the burr, each cutting element extending outwardly as the torsion springs are twisted as the burr is rotated.

* * * * *